(12) United States Patent
Vromen

(10) Patent No.: US 7,101,563 B1
(45) Date of Patent: Sep. 5, 2006

(54) MICRONIZED VITAMIN C FORMULATION

(75) Inventor: Jacob Vromen, Botany (AU)

(73) Assignee: Australian Importers, Ltd., Henderson, NV (US)

( * ) Notice: Subject to any disclaimer, the term of this patent is extended or adjusted under 35 U.S.C. 154(b) by 0 days.

(21) Appl. No.: 09/518,554

(22) Filed: Mar. 3, 2000

(51) Int. Cl.
*A61K 6/00* (2006.01)
*A61K 9/14* (2006.01)

(52) U.S. Cl. ...................... 424/401; 424/489
(58) Field of Classification Search ............... 424/401, 424/474, 489; 514/474
See application file for complete search history.

(56) References Cited

U.S. PATENT DOCUMENTS

| | | | |
|---|---|---|---|
| 3,743,708 A | | 7/1973 | Chase et al. |
| 4,938,969 A | | 7/1990 | Schinitsky et al. |
| 5,140,043 A | | 8/1992 | Darr et al. |
| 5,308,621 A | * | 5/1994 | Taylor et al. |
| 5,441,740 A | * | 8/1995 | Ozlen |
| 5,843,411 A | * | 12/1998 | Hernandez et al. |
| 6,146,664 A | * | 11/2000 | Siddiqui |
| 6,238,683 B1 | | 5/2001 | Burnett et al. ............... 424/405 |

FOREIGN PATENT DOCUMENTS

| | | | |
|---|---|---|---|
| WO | WO 93/00015 | * | 1/1993 |
| WO | WO 98/23152 | | 6/1998 |
| WO | WO00/02535 | | 1/2000 |
| WO | WO00/06155 | | 2/2000 |
| WO | WO01/03664 | | 1/2001 |

OTHER PUBLICATIONS

Australian Importers, Ltd. invoice dated Jul. 29, 1998.
Confidentiality, Non-Disclosure and Non-Use Agreement dated Jun. 17, 1998.
Letter dated Apr. 23, 1999 from Ronald G. Wheeland, M.D., to Mr. Scott Shapiro.
Letter dated Mar. 1, 1999 from Ronald G. Wheeland, M.D., to Mr. Scott Shapiro.
Letter dated Apr. 22, 1999 from Mark G. Rubin, M.D., to Mr. Scott Shapiro.
Supplemental European Search Report (Mailing Date Mar. 14, 2003).

* cited by examiner

*Primary Examiner*—Humera N. Sheikh
(74) *Attorney, Agent, or Firm*—Keown & Associates

(57) ABSTRACT

Stable vitamin C (L-ascorbic acid) compositions for topical application, comprising micronized L-ascorbic acid in a substantially non-aqueous carrier having a pH greater than that of skin, and preferably not lower than approximately 5.5 and not greater than approximately 7.5, are described. The composition may further comprise papain as an enzymatic exfoliant in addition to humectants, emollients, viscosity-increasing agents, surfactants, and preservatives. Methods of preparing the micronized L-ascorbic acid for use in the described formulations, by a "wet" micronization process, are also described. The compositions are useful as UV protectants, promoters of collagen synthesis and in the removal and/or treatment of wrinkles.

17 Claims, No Drawings

MICRONIZED VITAMIN C FORMULATION

BACKGROUND OF THE INVENTION

1. Field of the Invention

The present invention relates to stable ascorbic acid compositions or formulations and methods of use. More particularly, the invention relates to novel, micronized L-ascorbic acid (vitamin C) compositions for topical application, said compositions having a pH that is basic relative to the pH of skin, and being useful as collagen production stimulators, as antioxidants and/or as ultraviolet (UV) protectants.

2. Description of the Related Art

Ascorbic acid (vitamin C) and its derivatives are not endogenously produced and must be obtained from dietary sources. Ascorbic acid is a major cellular antioxidant and is known to promote collagen expression, wound healing and, when applied topically, is capable of protecting the skin against ultraviolet (UV) light exposure, although it is not a sunscreen. See, e.g., Colvon, R. M. & Pinnell, S. R., "Topical Vitamin C in Aging" in *Clinics in Dermatology, Skin Aging, and Photoaging*, Antonio Ledo. ed., 14 227–234 (1996); Shindo et al., *J. Invest. Dermatol.*, 102, 470–75 (1994); Freiberger, H. et al., *J. Invest. Dermatol.* 75, 425–30 (1980). However, ascorbic acid, and particularly L-ascorbic acid, is unstable in currently commercially available pharmaceutical vehicles for topical delivery to the skin. This instability leads to loss of potency and discoloration which may be due to oxidation of the L-ascorbic acid. In addition, L-ascorbic acid tends to hydrolyze when exposed to water, so is not stable in aqueous formulations or aqueous delivery vehicles.

Currently commercially available, topical L-ascorbic acid formulations therefore have associated disadvantages including, for example, instability, insufficient or less than optimal L-ascorbic acid concentrations, and the need for relatively low pH, typically from approximately 2.0 to approximately 3.0, which is acidic relative to the typical pH of skin, which is approximately 4.5 to approximately 5.0. Such low pH formulations promote skin irritation and require the presence of significant amounts of water, the presence of which tends to limit the ability of the ascorbic acid formulation to penetrate the skin.

There is, accordingly, a need for a stable topical ascorbic acid formulation which has sufficient ascorbic acid concentration, exhibits good skin penetration and is non-irritating. The present invention provides such formulations in a variety of embodiments.

SUMMARY OF THE INVENTION

A composition for topical use comprising greater than 25% L-ascorbic acid, by weight, and a non-aqueous carrier, wherein said composition has a pH greater than that of skin is described. The composition may preferably comprise greater that approximately 25% micronized L-ascorbic acid, by weight. The L-ascorbic acid has a mean particle size of preferably no greater than approximately 5 µm, more preferably no greater than approximately 2 µm, and most preferably between approximately 0.01 µm and 1 µm. The composition preferably comprises greater that 30% ascorbic acid, by weight, more L-ascorbic acid than D-ascorbic acid, by weight, more L-ascorbic acid than ascorbic acid derivatives, and is most preferably essentially free of D-ascorbic acid, and is essentially free of ascorbic acid derivatives. The pH of the composition is preferably at least about 5.5, at least about 6.0, or at least about 7.0. The composition may further comprise an enzymatic exfoliant, preferably papain. The non-aqueous carrier is preferably glycerin. The L-ascorbic acid is preferably micronized via a "wet" micronization process in oil that is, preferably, derived from plant materials, and more preferably, comprises, at least in part, capric/caprylic triglycerides. Also provided is a method of providing one or more of the following treatments to a mammal, preferably a human, in need of such treatment: UV protection, removal and prevention of wrinkles, or stimulating collagen production, comprising, identifying a mammal in need of such treatment, and topically applying the composition described herein to said mammal.

DETAILED DESCRIPTION OF THE PREFERRED EMBODIMENTS

Topical L-ascorbic acid transdermal formulations are disclosed which have superior L-ascorbic acid concentrations, skin penetration characteristics, are relatively highly stable in storage and/or are non-irritating, when compared to currently commercially available topical L-ascorbic acid formulations. The topical formulations are relatively well tolerated on even the most sensitive skin, e.g., the skin near to and around the eyes. Currently commercially available topical ascorbic acid formulations warn against and have been shown to cause significant irritation problems and are therefore not to be recommended for use near and around the eyes. The compositions and formulations described herein are useful in one or more of a variety of manners, as described herein, and in various embodiments for topical administration to effect the following: UV protection, removal and prevention of wrinkles, and stimulation of collagen production, and other topical uses known in the art. See, e.g., Colvon, R. M. & Pinnell, S. R., "Topical Vitamin C in Aging" in *Clinics in Dermatology, Skin Aging, and Photoaging*, Antonio Ledo. ed., 14 227–234 (1996); Shindo et al., *J. Invest. Dermatol.*, 102, 470–75 (1994); Freiberger, H. et al., *J. Invest. Dermatol.* 75, 425–30 (1980), and references cited therein.

Preferably, the compositions and formulations are to be applied directly to the skin once per week, once per day, twice per day or three times per day. Alternatively, the compositions and formulations may be applied directly to the skin less frequently or only on specific occasions, for example, before extended exposure to UV irradiation, to achieve certain of the benefits described herein. The quantity and extent of application will vary with the particular result desired or condition to be treated. Such preferred application will vary from about 0.1 mg per $cm^2$ skin per day to 50 mg per $cm^2$ skin per day, massaged into the skin, as will be appreciated by those of skill in the art.

L-ascorbic acid, in contrast to D-ascorbic acid and various ascorbic acid derivatives and racemic mixtures thereof, is the only form of ascorbic acid that the mammalian body, especially the primate and most especially the human body, can directly utilize. The other compounds (e.g., D-ascorbic acid and ascorbic acid derivatives) must first be converted to L-ascorbic acid in vivo. The topical formulations described herein preferably comprise at least 25% L-ascorbic acid. In a preferred embodiment, the formulations comprise at least about 26%, 27%, 28%, 29%, 30%, 35%, 40%, 45%, 50% or more L-ascorbic acid, by weight. In preferred embodiments, the formulation comprises L-ascorbic acid (Vitamin C) and is substantially free of D-ascorbic acid. In other preferred embodiments, the formulation comprises L-ascorbic acid (Vitamin C) and is substantially free of the chemical derivatives of ascorbic acid. In yet other preferred embodiments, the formulation comprises L-ascorbic acid (Vitamin C) and is substantially free of both D-ascorbic acid and of the chemical derivatives of ascorbic acid.

L-absorbic acid in powder form is preferred. The L-ascorbic acid powder may be converted into the desired particulate size state by conventional methods, e.g by grinding the powder, in coarse particle form, in the presence of suitable grinding aids and using known grinding apparatus, e.g., a jet, ball, vibration or hammer mill, preferably a high speed stirring mill or impact mill, especially a rotating ball mill, vibrating mill, tube mill or rod mill.

According to the preferred method of manufacturing the preferred formulations, L-ascorbic acid in powder form is subjected to a "wet" micronization process, as made available by Microniser Pty. Ltd. of Dandenong, Australia/Micronisers of Australia of Melbourne, Australia. This process, which may be contrasted to so-called "dry" or standard micronization processes, preferably involves the grinding of the powder, suspended in or otherwise in the presence of a non-aqueous liquid, preferably an oil (hereinafter, the "suspending oil"). The process is preferably conducted in an abrasion-resistant container in the presence of a grinding medium, using sufficiently high rpm for a sufficiently long duration, and a suitable stirrer. The resulting suspension may separated from the grinding medium by suction filtration of the powder. This micronization process is capable of producing particles of L-ascorbic acid having a mean particle size corresponding to the molecule size of L-ascorbic acid.

Alternatively, the grinding may be conducted in the presence of 0.1 to 30%, and preferably 0.5 to 15% by weight, of a grinding aid such as an alkylated vinylpyrrolidone polymer, a vinylpyrrolidone-vinylacetate copolymer, an acylglutamate, an acrylate-tert.-octylpropenamide copolymer, a ditolylether sulphonic acid-formaldehyde condensate, a Carbomer, a commercial mixture of fatty acid esters comprising a nonionic precurser such as tristyrylphenol ethoxylate or, in particular, a phospholipid, as described in U.S. Pat. No. 5,869,030, the complete description of which is hereby incorporated by reference herein.

The suspending oil is most preferably a vegetable oil, which promotes (along with the physical micronization process, as described above) breaking the ascorbic acid into ultrafine particles and, at the same time, coats the particles with the oil, which promotes maximum absorbance and stability of the L-ascorbic acid in the formulation. The micronized L-ascorbic acid particles used preferably exhibit a mean particle size of no more than approximately 5 µm, and preferably a mean particle size of in the range of from about 0.01 to about 2 µm, and most preferably from about 0.05 to about 1.5 µm, and especially from about 0.1 to about 1.0 µm.

Oils most preferable and therefor most suitable for use include caprylic triglycerides, capric triglycerides, isostearic triglycerides, adipic triglycerides, propylene glycol myristyl acetate, lanolin oil, polybutene, isopropyl palmitate, isopropyl myristate, diethyl sebacate, diisopropyl adipate, hexadecyl stearate, cetyl oleate, oleyl alcohol, hexadecyl alcohol, wheatgerm oil, vegetable oils such as castor oil, corn oil, cottonseed oil, olive oil, palm oil, coconut oil, palm kernel oil, canola oil, safflower oil, jojoba oil, hydrogenated vegetable oils, mineral oil and silicone oils. In a preferred embodiment, the ascorbic acid is micronized in the presence of capric/caprylic glycerides in which the L-ascorbic acid is present in an amount from 70% to 80%, by weight.

The wet micronization process described above is preferable over the more conventional dry micronization of ascorbic acid because the heat generated in such dry micronization process typically results in chemical breakdown or oxidation of ascorbic acid. In contrast, the wet micronization process allows preparation of a more stable ascorbic acid formulation useful, especially for topical application.

In a preferred embodiment of the present invention, the topical ascorbic acid preparations are formulated with a non-aqueous (i.e., anhydrous) base. Anhydrous bases suitable for use include silicones, esters, amides, ethoxylated fats, mineral oil, petrolatum, vegetable oils, animal fats, triglycerides, polyols (e.g., glycerol), glycerin, propylene glycol and sorbitol.

In a particularly preferred embodiment, the anhydrous base is glycerin, which is a superior, naturally occurring humectant (i.e., moisturizer) and is found in living systems. The use of glycerin, as opposed to an aqueous base such as water, or the use of one or more other humectants found in living systems, facilitates the incorporation of the formulation, and of the L-ascorbic acid found therein, into the skin and into the subsurface skin. In another preferred embodiment, the anhydrous base is between about 1% and 50%, more preferably between about 10% and 45%, more preferably between about 20% and 40%, and most preferably 35% by weight of the formulation.

In another preferred embodiment, the topical ascorbic acid preparations or formulations have a pH that is basic relative to the pH of skin (typically ranging from approximately 4.5 to approximately 5.0), and preferably a pH that is not lower than approximately 5.5 and not higher than about 7.0, i.e., the formulation preferably have a slightly acid to neutral pH. Most preferably, the formulations have a pH greater than approximately 6.0 and less than approximately 7.5. Most currently commercially available topical ascorbic acid formulations exhibit acidic pHs in the range of approximately 2.0 to approximately 3.0, which tend to irritate the skin and are therefore not desirable. Preferred embodiments tend to avoid this undesirable aspect while providing one or more of the advantages recited herein.

The topical formulations described herein may further comprise an agent, preferably an enzyme or other non-acid agent, which promotes removal of the stratum corneum and therefore promotes deeper penetration of the ascorbic acid into subsurface skin. Thus, such an enzyme acts as an exfoliant, removing only the dead cell layer of the skin causing no damage to the underlying living cell layers. Currently commercially available exfoliants, including alpha hydroxy acids (AHAs), beta hydroxy acids (BHAs) and retinoids tend to cause adverse topical reactions including but not limited to skin irritation, erythema and blistering. One preferred enzyme for use in the formulations is papain, an enzyme obtainable from unripe papaya fruit. One particularly preferred form of papain is Linked-Papain™ (papain carbomer, as described in CTFA, the International Cosmetic Ingredients Dictionary) in which papain is covalently immobilized to 1% polyacrylic acid (900,000 daltons), commercially available from Collaborative Laboratories, 3 Technology Drive, East Setauket, N.Y. 11733. In a preferred embodiment, the enzyme is present in the formulation in an amount between about 1% and 10%, more preferably between about 1.5% and 6%, and between about 2% and 5%, most preferably about 4% by weight.

The ascorbic acid compositions manufactured by the wet micronized process described herein may be formulated for topical application with pharmaceutically acceptable carriers using methods well known in the cosmetic and pharmaceutical arts, including gels, creams, ointments, emulsions, dispersions, salves, pastes, lotions and the like. These formulations may additionally comprise one or more emulsifiers, humectants (e.g., glycerin, glycerol, sorbitol and other polyols), skin conditioning agents (e.g., propylene glycol, sweet almond oil, apricot kernel oil), surfactants (e.g., ceteth-20), colorants such as staining dyes and pigments (e.g., calcium, barium and aluminum lakes, iron oxides, titanium dioxide and mica), antioxidants (i.e., tocopherols, retinoids, ascorbyl palmitate, thiodipropionic acid), viscosity-enhancing agents (e.g., cetearyl alcohol, polyethylene glycol Myristyl, Cetyl alcohol), optional, additional vitamins, optional, additional minerals, emollients (e.g., paraffin liquid, polysorbate-60), skin conditioning agents (e.g., propylene glycol, sweet almond oil), biological additives (e.g., botanicals and herbals), UV absorbs for use as sunscreens (e.g., octyl methoxycinnamate, butyl methoxydibenzolylmethane, oxybenzone), germicides (e.g., antibotics, Tricolsan), preservatives (e.g., BHA, BHT, methylparaben, ethylparaben, propylparaben, butylparaben, octhilinone) and fragrances (e.g., strawberry extract, *mangifera indica*). It will be appreciated by those of skill in the art that particular compounds may be properly classified in one, or two or more of the above-listed classifications or compound types.

Emulsifiers contemplated for use include but are not limited to monoacyl glycerol, such as glyceryl monoalkanoates; glyceryl monoalkenoates; diacyl 1,2- or 1,3-disubstituted) glycerol, such as glyceryl dialkanoates, glyceryl dialkenoates and polyglyceryl esters; cetyl alcohol, stearic acid, sorbitan stearate and oleates.

Examples of botanicals and herbals include but are not limited to *gingko biloba* extract, tea tree oil, chamomile extract, *echinacea* extract, *aloe* extract, *calendula officinalis* extract, *hydrocotyl* extract, *hypericum perforatum* extract, *mimosa tenuiflora* extract, *carica papaya* extract, *betula alba* extract, *cucumis sativus* extract, *panax ginseng* extract, *aesculus hippocastanum* extract, *Tilia cordata* extract, *propolis cera* extract, and the like.

In a preferred embodiment, one or more skin conditioning agent(s) is present in the formulation in a combined amount of from about 5% to 25% by weight, more preferably from about 10% to 20% by weight, and most preferably from about 16% to 19% by weight.

In a preferred embodiment, one or more emollients is present in the formulation in a combined amount of from about 1% to 10% by weight, more preferably about 5% to 8% by weight, and most preferably about 6% by weight.

One or more viscosity increasing agents is preferably present in the formulations in an amount from about 2% to 10% by weight, preferably about 4% to 6% by weight.

In another preferred embodiment, one or more surfactants may be present in the formulation in an amount from about 1% to 5% by weight, and most preferably about 2.5% weight.

One or more antioxidants, in addition to L-ascorbic acid described above, may also be present in a combined amount of between about 1% and 10% by weight, and most preferably about 5% by weight.

One or more preservatives may be present in a combined amount of between about 0.1% and 5% by weight, and most preferably about 0.5% by weight.

The compositions may also include one or more biological additives, such as botanicals or herbals. As used herein, the term "biological additive" indicates any compound obtained from a natural source, including plants, animals, bacteria and yeast, which has a medicinal or otherwise beneficial effect when topically applied to the skin. Examples of biological additives include oil of *Melaleuca alternifolia*, oil of *Lavandula angustifolia*, *Carica papaya* extract, *Echinacea angustifolia* extract, *Mimosa tenuiflora* extract, *Hydrocotyl (centella) asiatica* extract, *gingko biloba* extract, oil of *Melaleuca alternifolia* (tea tree oil), *Matricaria chamomila* (chamomile) extract, *Hypericum perforatum* extract, *Aloe barbedensis* extract, and the like. The biological sources for "biological additive" may also include, but are not limited to the following: *Aloe Vera, Aloe Barbedensis; Arnica, Arnica Montana*; Bladderwrack (seaweed), *Fucus Vesciculosis*; Birch, *Betula Alba (Pendula)*; Chamomile, *Matricaria Chamomila (Chamomila Recutita)*; Marsh Mallow, *Althea Officinalis*; Meadow Sweet, *Spirea Ulmaria (Filipendula)*; Mint/Lemon Balm, *Melissa Officinalis; Mimosa, Mimosa Tenuiflora*; Myrrh Tincture, *Commiphor Myrrha*; Neem, *Melia Azadirachta*; Nettle (stinging), *Urtica Dioica; Papaya, Carica Papaya*; Propolis (bee glue), *Propolis Cera*; Raspberry, *Rubis Idaeus*; Red Poppy, *Papaver Rhoeas*; Rose Hip (dog rose), *Rosa Carima*; Rosemary, *Rosemarinus Officinalis*; Sage, *Salvia Officinalis*; St. Johns Wort, *Hypericum Perforatum*; Strawberry, *Fragaria Vesca; Thea Sinensis* (green tea), *Camelia Sinensis*; Walnut, *Juglans Regia*; Witchhazel (dist/extr), *Hamamelis Virginiana*; Yarrow, *Achillea Millefolium*; Wild Yam, *Dioscorea Villosa*; Hawthorn, *Crataegus Monogina/Oxyantha*; Herma (black/rod), *Lawsoma Ehemus*; Hops, *Humulus Lupulus*; Horse Chestnut, *Aesculus Hippocastanum*; Horse Tail, *Equisitum Arvense*; Ivy, *Hedera Helix*; Linden/Lime Tree Blossoms, *Tilia Argentea Cordata*; Madder, *Rubia Tinctorum*; Marigold, *Calendula Officinalis; Centella Asiatica, Centella Asiatica* Urban (*hydrocotyl Asiatica*); Carrot (roots), *Daucus Carota*; Comfrey (Allantoine), *Symphytum Officinale*; Coneflower (*Echinacea*), *Echinacea Angustifolia*; Cucumber, *Cucumis Sativus (Frucus Cucumis)*; Fenugreek, *Trigonella Foenum Greacum; Gingko, Gingko Biloba; Ginseng, Panax Ginseng*; Great Burdock, Radix Bardanea/*Arctium Lappa*; Tea Tree Oil, Oil of *Melaleuca Alternifolia*; Colts Foot, *Tussilago Farfara*; Clover, *Trifolium Pratense*; Speedwell, *Veronica Officinalis*.

Further biological additives, along with the biological or medicinal properties of the biological additives described herein and of other known biological additives are know to those of skill in the art. References, including encyclopedias and treatises, known to those of skill in the art, that described such biological additives, along with the biological or medicinal properties of the biological additives described herein, include: Guenther—The Essential Oils, Van Nostrand; Int. Cosmetic Ingredient Dictionary, Vol 1 & 2, C.T.F.A. 1995; Int. Cosmetic Ingredient Handbook, C.T.F.A. 1995; British Herbal Pharmacopoeia, British Herbal Medicine Assoc., 1983; Clinical Applications of Ayurvedic & Chinese Herbs, K. Bone, Phytotherapy Press, 1996; A Handbook of Chinese Healing Herbs, D. Reed, Shambala, Boston, 1995; *Echinacea*—Nature's Immune Enhancer, S. Foster, Healing Arts Press, Rochester, 1991; Encyclopedia of Herbs, D. Brown, RD Press, 1995; Encyclopedia of Medicinal Plants, A. Chevalier, Dorling Kingers Ley, 1996; L'Angelica—Herbal Extracts; Cosmetochem —Herbasol Extracts. These references are incorporated herein in their entirety.

EXAMPLES

The following examples are illustrative, but not limiting, of the novel ascorbic acid formulations for topical use.

Example 1

A preferred cream formulation was prepared. The components of this formulation, and their respective percentages, by weight, are listed in Table 1. As noted above, many of the components of the formulation, as listed in Table 1, are not necessarily elements of the formulation of the present invention. Only as recited in the claims, or as explicitly recited in the written description, are particular components necessary components of the formulation of the present invention.

TABLE 1

L-ascorbic acid cream formulation

| COMPOUND | APPROX. WEIGHT % | TYPE OF COMPOUND |
|---|---|---|
| L-ascorbic acid | 25 | antioxidant |
| glycerin | 35 | humectant |
| propylene glycol | 10 | skin conditioning agent |
| capric-caprylic triglyceride | 6 | emollient |
| myristyl alcohol | 2 | viscosity increasing agent |
| cetearyl alcohol | 3 | viscosity increasing agent |
| papain carbomer | 4 | exfoliant |
| ceteth-20 | 2.5 | surfactant/solubilizer |
| α-tocopherol | 3 | antioxidant/skin conditioning agent |
| apricot kernel oil | 2 | skin conditioning agent |
| sweet almond oil | 3 | skin conditioning agent/biological additive |
| ascorbyl palmitate | 1 | antioxidant |
| thiodipropionic acid | 0.5 | antioxidant |
| BHT | 0.5 | antioxidant |
| methyl/ethyl/propyl/butyl parabens in phenoxyethanol | 0.5 | preservative |
| strawberry extract | 0.2 | biological additive/fragrance |

The compounds listed in Table 1 may be obtained from any of numerous commercial sources, and are preferably obtained from suppliers that provide the compounds in conditions that satisfy the specification of the CTFA, International Cosmetic Ingredients Dictionary.

Example 2

A preferred cream formulation was prepared in the following manner: (1) the following ingredients were heated at approximately 65–70° C. until a homogeneous mixture was observed: ceteth 20, cetearyl alcohol, myristyl alcohol, almond oil, apricot kernel oil, BHT, α-tocopherol, propylene glycol; (2) while agitating the mixture, the following ingredients were added slowly: glycerol (aqueous phase), (3) when an emulsion was detected, the following ingredients were added while mixing: ascorbyl palmitate; thioproprionic acid; (4) the mixture was stirred until homogeneous, and the following ingredients were added at 45° C.: micronized L-ascorbic acid in capric/caprylic triglyceride; (5) the following preservative and additives were then added methyl/ethyl/propyl/tutyl parabens in phenoxyethanol and strawberry extract; (6) the papain carbomer was add at approximately 30–35° C.

Example 3

Another embodiment of preferred cream formulation is prepared. The components of this formulation, and their respective percentages, by weight, are listed in Table 2. As noted above, many of the components of the formulation, as listed in Table 2, are not necessarily elements of the formulation. Only as recited in the claims, or as explicitly recited in the written description, are particular components necessary components of the formulation of the present invention.

TABLE 2

L-ascorbic acid cream formulation

| COMPOUND | APPROX. WEIGHT % | TYPE OF COMPOUND |
|---|---|---|
| L-ascorbic acid | 30 | antioxidant |
| glycerin | 35 | humectant |
| propylene glycol | 15 | skin conditioning agent |
| capric-caprylic triglyceride | 6 | emollient |
| cetearyl alcohol | 5 | viscosity increasing agent |
| papain carbomer | 6 | exfoliant |
| ceteth-20 | 2.5 | surfactant/solubilizer |
| α-tocopherol | 3 | antioxidant/skin conditioning agent |
| apricot kernel oil | 3 | skin conditioning agent |
| sweet almond oil | 1 | skin conditioning agent/biological additive |
| ascorbyl palmitate | 1 | antioxidant |
| methyl/ethyl/propyl/butyl parabens in phenoxyethanol | 0.5 | preservative |
| strawberry extract | 0.2 | biological additive/fragrance |

The compounds listed in Table 2 may be obtained from any of numerous commercial sources, and are preferably obtained from suppliers that provide the compounds in conditions that satisfy the specification of the CTFA, International Cosmetic Ingredients Dictionary.

Example 4

Another preferred cream formulation is prepared in the following manner: (1) the following ingredients are heated at approximately 65–70° C. until a homogeneous mixture is observed: ceteth 20, cetearyl alcohol, almond oil, apricot kernel oil, BHT, α-tocopherol, propylene glycol; (2) while agitating the mixture, the following ingredients are added slowly: glycerol (aqueous phase), (3) when an emulsion is detected, the following ingredients are added while mixing: ascorbyl palmitate; (4) the mixture is stirred until homogeneous, and the following ingredients are added at 45° C.: micronized L-ascorbic acid in capric/caprylic triglyceride; (5) the following preservative and additives are then added methyl/ethyl/propyl/tutyl parabens in phenoxyethanol and strawberry extract; (6) the papain carbomer is add at approximately 30–35° C.

Although the foregoing invention has been described in detail by way of illustration and examples for purposes of clarity of understanding, it is readily apparent to those of ordinary skill in the art in light of the teachings of this invention that certain changes and modifications, particularly with regard to specific exemplary components and to the specific ranges of the components of the formulations, may be made thereto without departing from the spirit and scope of protection afforded the present invention described, and claimed, herein.

What is claimed is:

1. A method of providing one or more of the following treatments to a mammal in need of such treatment: UV protection, decrease or alleviation of wrinkles, or stimulating collagen production in a mammal, said method comprising,
   identifying a mammal in need of such treatment, and
   topically applying to said mammal a composition comprising at least 30% L-ascorbic acid, by weight, micronized in an oil selected from the group consisting of caprylic triglycerides, capric triglycerides, isostearic triglycerides, adipic triglycerides, propylene glycol myristyl acetate, lanolin oil, polybutene, isopropyl palmitate, isopropyl myristate, diethyl sebacate, diisopropyl adipate, hexadecyl stearate, cetyl oleate, oleyl alcohol, hexadecyl alcohol, wheatgerm oil, vegetable oils such as castor oil, corn oil, cottonseed oil, olive oil, palm oil, coconut oil, palm kernel oil, canola oil, sunflower oil, safflower oil, meadow foam oil, jojoba oil, hydrogenated vegetable oils, and mineral oil, a non-aqueous carrier selected from the group consisting of esters, amides, ethoxylated fats, mineral oil, petrolatum, vegetable oils, animal fats, triglycerides, polyols including glycerol, propylene glycol, glycerin and sorbitol, and an exfoliant, wherein the mean particle size of the L-ascorbic acid is no greater than approximately 5 µm.

2. The method of claim 1, wherein said mammal is human.

3. The method of claim 1, wherein said L-ascorbic acid has a mean particle size of no greater than approximately 2 µm.

4. The method of claim 1, wherein said L-ascorbic acid has a mean particle size between approximately 0.01 µm and 1 µm.

5. The method of claim 1, wherein said composition comprises greater than 35% L-ascorbic acid.

6. The method of claim 1, wherein said composition comprises, by weight, more L-ascorbic acid than D-ascorbic acid.

7. The method of claim 1, wherein said composition comprises, by weight, more L-ascorbic acid than ascorbic acid derivatives.

8. The method of claim 1, wherein said composition is essentially free of D-ascorbic acid, and is essentially free of ascorbic acid derivatives.

9. The method of claim 1, wherein said exfoliant is an enzyme.

10. The method of claim 9, wherein said enzymatic exfoliant comprises papain.

11. The method of claim 1, wherein said non-aqueous carrier comprises glycerin.

12. The method of claim 1, wherein said oil may be derived from plant materials.

13. The method of claim 1, wherein said oil comprises capric/caprylic triglycerides.

14. The method of claim 1, wherein said L-ascorbic acid is prepared by a wet micronization process.

15. The method of claim 1, wherein the composition is prepared by a method comprising micronizing ascorbic acid powder in an oil.

16. The method of claim 15, wherein said oil is derived from plant materials.

17. The method of claim 15, wherein said oil comprises capric/caprylic triglycerides.

* * * * *